United States Patent [19]

Higaki et al.

[11] 4,428,885
[45] Jan. 31, 1984

[54] ESTERIFICATION REACTION PRODUCTS

[75] Inventors: Yuzo Higaki, Machida; Osamu Yamada, Yokohama, both of Japan

[73] Assignee: The Nisshin Oil Mills, Ltd., Tokyo, Japan

[21] Appl. No.: 294,567

[22] Filed: Aug. 20, 1981

[30] Foreign Application Priority Data

Sep. 1, 1980 [JP] Japan ................ 55-119872

[51] Int. Cl.$^3$ .............................. C11C 3/02
[52] U.S. Cl. .................. 260/410.9 N; 424/312; 424/358; 424/64
[58] Field of Search .................. 260/410.9 N

[56] References Cited

U.S. PATENT DOCUMENTS

| | | | |
|---|---|---|---|
| 2,218,439 | 10/1940 | Rothrock | 260/410.9 N X |
| 2,273,891 | 2/1942 | Pollack et al. | 260/410.9 N X |
| 2,356,871 | 8/1944 | Moffett et al. | 260/410.9 N X |
| 2,374,081 | 4/1945 | Tattershall | 260/410.9 N X |
| 2,384,117 | 9/1945 | Muskat et al. | 260/410.9 N X |
| 2,384,126 | 9/1945 | Muskat et al. | 260/410.9 N X |
| 2,385,931 | 10/1945 | Muskat et al. | 260/410.9 N X |
| 2,385,934 | 10/1945 | Muskat et al. | 260/410.9 N X |
| 2,475,557 | 7/1949 | Swern et al. | 260/410.9 N X |
| 2,476,341 | 7/1949 | Weber | 260/410.9 N X |
| 2,516,928 | 8/1950 | Swern | 260/410.9 N X |
| 2,531,275 | 11/1950 | Jones | 260/410.9 N |
| 2,692,256 | 10/1954 | Bauer et al. | 260/410.9 N X |
| 3,179,641 | 4/1965 | Brown et al. | 260/410.9 N X |
| 3,520,839 | 7/1970 | Milligan et al. | 260/410.9 N |

*Primary Examiner*—Helen M. S. Sneed
*Attorney, Agent, or Firm*—Bucknam and Archer

[57] ABSTRACT

A new esterification reaction product is obtained by an esterification reaction between an intermolecular oligo-esterification carboxylic acid of 12-hydroxy stearic acid and/or ricinoleic acid and sterol. Also, a mixture of a sterol ester of the oligo-esterification carboxylic acid and a sterol ester of the above fatty acid is obtained by reacting directly 12-hydroxy stearic acid and/or ricinoleic acid with sterol.

These esterification reaction products have a good emulsifying property, hydrating property and moisture retaining property and are useful for an oil base of cosmetics and endermic liniments.

1 Claim, No Drawings

ESTERIFICATION REACTION PRODUCTS

BACKGROUND OF THE INVENTION

This invention relates to a new esterification reaction product and cosmetic and endermic liniments containing same.

Various esters are used for an oil base of the skin or hair cosmetics and endermic liniments. It is, for example, known that stearic acid esters or oleic acid esters of cholesterols can be used for stick-like products such as lipsticks and eye shadows, creams and ointments (e.g. Japanese Application Kokai No. 52-79030 and Japanese Patent Publication No. 39-9297). These esters have a comparatively improved emulsifying property and hydrating property, however, it is desirable to further improve these properties to enhance performances of cosmetics and endermic liniments.

SUMMARY OF THE INVENTION

An object of this invention is to provide a new esterification reaction product improved in the emulsifying property, hydrating property and moisture retaining property.

Another object of this invention is to provide cosmetics and endermic liniments containing these esterification reaction products as an oil base.

In accordance with this invention there are provided esterification reaction products between an intermolecular oligo-esterification carboxylic acid of 12-hydroxy stearic acid and/or ricinoleic acid represented by the formula,

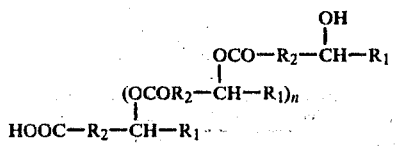

wherein radical

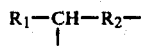

stands for the alkyl group of 12-hydroxy stearic acid or ricinoleic acid wherein $R_1$ is $-(CH_2)_5CH_3$ and $R_2$ is $-(CH_2)_{10}$ or $-(CH_2)_7CH=CHCH_2^-$ and n is 0 or an integer of 1 or more and sterol.

DETAILED DESCRIPTION OF THE INVENTION

According to this invention, when an oligo-esterified carboxylic acid obtained by an intermolecular esterification reaction between hydroxyl groups and carboxyl groups present in the molecule of 12-hydroxy stearic acid and/or ricinoleic acid is used as a fatty acid, esters thereof with sterol are obtained with remarkably improved emulsifying property, hydrating property and moisture retaining property as compared with sterol esters of conventional fatty acids.

Though the upper limit of n in the above formula is not particularly restricted, it is, preferably, about 10 and may be more than 10 in case of conducting the reaction under severer conditions.

12-Hydroxy stearic acid and ricinoleic acid used in this invention are a fatty acid containing one hydroxyl group in the molecule, which is derived from castor oil.

Sterols which may be used are, for example, cholesterol distributed widely in animal cells and phytosterols distributed in the vegetable kingdom e.g. soybean oil and others. In addition, methylsterols containing a methyl group in the sterol nucleus and hydrogenated products thereof may be used.

The new esterification reaction products of this invention may be prepared by subjecting 12-hydroxy stearic acid and/or ricinoleic acid to an intermolecular esterification reaction according to conventional methods in the absence of or in the presence of a catalyst (e.g. tin chloride) to obtain desired oligo-esterified carboxylic acid and thereafter adding sterol in indicated amount to carry out an esterification reaction.

The intermolecular oligo-esterification reaction may be, in general, carried out under normal pressure or reduced pressure at temperatures of 160°-250° C. The degree of oligo-esterification or the number of n in the above formula may be adjusted in accordance with reduced degree of acid value.

In the intermolecular oligo-esterification reaction there are obtained internal condensation products in addition to the intermolecular esterification products, which may be allowed to remain in the reaction products or may be removed in the purification of end products by deodorizing with a high temperature steam.

Next, the esterification reaction between the oligo-esterified carboxylic acid and sterol may be carried out in conventional methods in the absence of or in the presence of a catalyst (e.g. tin chloride). The reaction temperature is, preferably, between 160° and 250° C. The mole ratio of the oligo-esterified carboxylic acid to the sterol is within the range of preferably, 1.0:1.5-1.5:1.0. In the intermolecular oligo-esterification reaction and the esterification reaction with sterol, both the end of reaction may be determined by the acid value.

Alternatively, 12-hydroxy stearic acid and/or ricinoleic acid may be directly reacted with sterol. The mole ratio of the acid to the sterol is within the range of 1.2:1.0 to 5.0:1.0. In this direct reaction there is obtained a mixture of sterol esters of the oligo-esterified carboxylic acid and sterol esters of conventional fatty acids. This mixture can contain the conventional fatty acid-sterol esters of up to 50 weight %.

The raw sterol ester thus obtained is purified in conventional method by filtering off from the catalyst, decoloring and deodorizing with steam stripping.

To the esterification product thus obtained are conventional ingredients and arbitrary additives added to prepare various cosmetics and endermic liniments.

The amount of the esterification product to be incorporated is not particularly limited, though it is in general within the range of 0.05-50 weight % based on the weight of the composition.

The sterol esterification products of this invention are light color, odorless and render a good touch and affinity to the skin without irritating the skin and further, are remarkably superior in emulsifying property, hydrating property and moisture retaining property to conventional sterol esters and accordingly, are useful for the oil base of cosmetics and endermic liniments.

In this way the esterification products of this invention which are improved in the emulsifying property and hydrating property can be substituted for a part or all of surface active agents which are being used in emulsification products such as creams and liquid creams. Therefore the problem of irritating the skin originating from the surface active agent is improved. Also, owing to the good emulsifying power, these esterification products may be used in general as surface active agents.

Further, with adjusting the degree of oligo-esterification in the oligo-esterified carboxylic acid there are provided esterification products of desired molecular weight which are in form of from liquid to paste and wax. The touch, lubricating property, gelling power, compatibility, viscosity and melting point may be adjusted depending on desired purposes.

This invention will be illustrated by the following non-limitative Examples.

EXAMPLE 1

Preparation of sterol esters and properties thereof

[I] Process a:

a-1 Preparation of oligo-esterified carboxylic acid:

400 g of 12-hydroxy stearic acid (neutralization value 180, hydroxyl value 158) were fed to a 1.0 l four-necked flask provided with a stirrer, a thermometer, a nitrogen gas inlet and a water separating apparatus. 0.3 weight % of tin chloride as a catalyst and 5 weight % of xylol as a refluxing solvent, based on the weight of the total feeds were added and reaction was carried out at 160°–250° C. under stirring. While measuring the acid value the reaction was conducted for seven hours till the acid value had reached 50 and 380 g of oligo-esterified carboxylic acid were obtained.

Similarly, various oligo-esterified carboxylic acids of 12-hydroxy stearic acid and ricinoleic acid were prepared by conducting reaction till indicated acid values had been obtained as set forth in Table 1.

a-2 Preparation of sterol esters:

To 380 g of the oligo-esterified carboxylic acid obtained in the step of a-1 were fed 173 g of cholesterol, 0.3% of tin chloride and 5% of xylol added and reaction was carried out at 160°–220° C. for 15 hours. After completion of the reaction purification was conducted by filtering off the catalyst, decolouring with activated clay and then deodorizing with steam stripping at 200°–250° C. under reduced pressure. A small amount of unreacted cholesterol was removed and 455 g of cholesterol ester were obtained (Sample No. 1).

Similarly, sterol esters of Sample No. 2– No. 4 and No. 6–No. 9 were obtained.

[II] Process b:

300 g (1.5 mols) of 12-hydroxy stearic acid, 386 g (1.0 mol) of cholesterol were fed to a 1.0 l flask together with 0.3 weight % of tin chloride and 5 weight % of xylol and reaction was conducted at 180°–250° C. for about 27 hours. After reaction the acid value was 0.5. The catalyst was filtered off, decolouring was conducted with activated clay and deodorizing was conducted with steam stripping at 200°–250° C. under reduced pressure. 550 g of the subject ester were obtained. This ester was a mixture of 55% of the oligo-esterified carboxylic acid-cholesterol ester and 45% of the 12-hydroxy stearic acid-cholesterol ester (Sample No. 5).

[III] Properties of sterol esters:

Sterol esters were tested in respect of acid value, saponification value, hydroxyl value and melting point. The results obtained are set forth in Table 1.

Further, miscibilities of each sample with liquid paraffin, squalene, olive oil, castor oil, isopropyl myristate and ceresin were measured. The results were all good.

Also, the hydrating property of the above samples was measured, which is set forth in Table 2.

For comparison, esters of conventional fatty acids with sterols and petrolatum were measured. The results obtained are set forth in Table 2.

TABLE 1

| | Composition of Sterol Esters | | | | | Properties | | | | |
|---|---|---|---|---|---|---|---|---|---|---|
| | Oligo-esterified carboxylic acid | | | | | | | | | |
| Sample No. | Fatty acid | Average molecular weight | Acid value | Sterols | Appearance | Acid value | Saponification value** | Hydroxyl value | Melting point °C. | Colour G |
| 1 | 12-OH St* | 1120 | 50 | Cholesterol | Light yellow paste | 0.5 | 90.1 | 34.1 | 28~38 | 4− |
| 2 | " | " | " | Phytosterol | Yellow paste | 0.3 | 78.5 | 35.0 | 33~43 | 6 |
| 3 | " | " | " | Methylsterol | Yellow paste | 0.8 | 81.5 | 32.5 | 31~39 | 6 |
| 4 | " | 1870 | 30 | Cholesterol | Light yellow paste | 0.2 | 88.2 | 23.5 | 29~35 | 4 |
| 5 | " | — | — | Cholesterol | Yellow solid | 0.3 | 90.2 | 61.4 | 34~51 | 7− |
| 6 | " | 1870 | 30 | Hydrogenated cholesterol | Light yellow solid | 0.5 | 89.5 | 48.7 | 37~48 | 3+ |
| 7 | Ricinoleic acid | 1170 | 48 | Cholesterol | Yellow liquid | 0.3 | 89.1 | 34.0 | — | 6+ |
| 8 | Ricinoleic acid | " | " | Phytosterol | Yellow liquid | 0.4 | 80.8 | 34.8 | — | 8− |
| 9 | 12-OH St + Ricinoleic acid (1:1 weight ratio) | 1120 | 50 | Cholesterol | Yellow paste | 0.4 | 89.2 | 33.9 | ~27 | 7 |

*12-Hydroxy stearic acid.
**Measured by adding 20 ml of a 1.0 N KOH-ethanol solution to a sample (1.5 ± 0.5 g) and saponifying while refluxing for 3 hours.

TABLE 2

| | Hydrating* property % | Hydrating property of a mixture of sterol ester with petrolatum, % | | |
|---|---|---|---|---|
| Samples | | 2%** | 6%** | 10%** |
| No. 1 | 850 | 280 | 390 | 510 |
| No. 2 | 520 | 190 | 240 | 290 |

TABLE 2-continued

| Samples | Hydrating* property % | Hydrating property of a mixture of sterol ester with petrolatum, % | | |
|---|---|---|---|---|
| | | 2%** | 6%** | 10%** |
| No. 3 | 590 | 240 | 320 | 410 |
| No. 4 | 930 | 330 | 450 | 550 |
| No. 5 | 720 | 240 | 330 | 480 |
| No. 6 | 510 | 220 | 280 | 340 |
| No. 7 | 680 | 250 | 330 | 430 |
| No. 8 | 410 | 110 | 190 | 270 |
| No. 9 | 790 | 280 | 370 | 460 |
| Cholesteryl-oleate | 80 | 40 | 50 | 50 |
| Phytosteryl-oleate | 60 | 20 | 30 | 30 |
| Methyl-cholesteryl oleate | 80 | 30 | 40 | 50 |
| Cholesteryl isostearate | 180 | 30 | 80 | 120 |
| Cholesteryl 12-hydroxy stearate | 380 | 160 | 210 | 250 |
| Phytosteryl 12-hydroxy stearate | 280 | 100 | 110 | 140 |
| Petrolatum | 8 | — | — | — |

*To 100 g of a sample is an ion-exchanged water added under stirring to form a w/o type emulsion. The hydrating property is indicated by a maximum amount of water added at which a w/o type emulsion can be formed.
**Weight ratio of the sterol ester to be incorporated into petrolatum.

As is apparent from the above Table, the esters of this invention (Sample No. 1–No. 9) are superior in the hydrating property to conventional esters of comparison examples and therefore, have a good emulsifying power.

Further, the esters of this invention are coated with average thickness of 5μ on a glass plate of 12 cm × 7 cm under a relative humidity of 80% at 25° C. and after allowing to stand for 200 hours, a moisture absorbing capacity was measured. The results are set forth in Table 3.

For comparison, esters of conventional fatty acids with sterol and lanolin were similarly measured.

TABLE 3

| Samples | Moisture absorbing capacity μg/cm² |
|---|---|
| No. 1 | 31.2 |
| No. 2 | 19.8 |
| No. 3 | 15.5 |
| No. 4 | 29.5 |
| No. 5 | 25.9 |
| No. 6 | 25.6 |
| No. 7 | 21.2 |
| No. 8 | 20.3 |
| No. 9 | 23.8 |
| Lanolin | 3.5 |
| Cholesteryloleate | 9.3 |
| Phytosteryloleate | 7.3 |
| Cholesteryl 12-hydroxystearate | 10.5 |
| Phytosteryl 12-hydroxystearate | 9.8 |

Table 3 shows that the sterol esters of this invention are superior in the moisture retaining property (twice or more) to those of the comparison examples.

Further, a primary irritant effect on the human body was examined by a closed patch test and as a result, none of the products of this invention (Sample Nos. 1–9) exhibited irritant effect on the skin.

The closed patch test: The horniness and sebum on the skin of the upper inner aspect of the arm were removed. The skin surface was covered with a cotton fabric of one inch square on which a sample was applied, and an oiled paper was covered thereon. Further, a paper adhesive plaster was covered in parallel crosses on the oiled paper and furthermore, a bandage was applied thereto. This test was effected on twenty persons of health and rating was conducted after 24 hours, 48 hours and one week, respectively.

EXAMPLE 2

Preparation of Cosmetics and Ointments

Cosmetics were prepared by incorporating conventional ingredients into the sterol ester of this invention.

Using samples No. 1–No. 9 as the sterol ester, other ingredients were incorporated to prepare cosmetics of Formulations No. 1–No. 5 and endermic liniment of Formulation No. 6. The cosmetics and endermic liniment obtained have good properties and performances.

| Formulation No. 1: | | |
|---|---|---|
| (A) | Oil phase | |
| | Liquid paraffin | 50 wt. % |
| | Bees wax | 15 wt. % |
| | Sample No. 2 | 5 wt. % |
| (B) | aqueous phase | |
| | Borax | 0.8 wt. % |
| | Water | balance |
| (C) | Perfumes | small amount |

The oil phase (A) was dissolved at 80° C., to which the aqueous phase (B) warmed to 80° C. was added slowly. After cooling to 55° C. perfumes were added to the mixture which was then cooled to 35° C. A cold cream was obtained.

| Formulation No. 2: | | |
|---|---|---|
| (A) | Oil phase | |
| | Stearic acid | 10.0 wt. % |
| | Sample No. 4 | 2.0 |
| | Sample No. 7 | 2.0 |
| | Olive oil | 8.0 |
| | Antioxidant (tocopherol) | small amount |
| (B) | Aqueous phase | |
| | Sodium lauroiminodipropionate | 6.0 |
| | Water | balance |

The oil phase (A) was dissolved uniformly at 80° C., to which the aqueous phase (B) warmed to 75° C. was added slowly and cooled to 35° C. under stirring. A nutritious cream was obtained.

| Formulation No. 3: | | |
|---|---|---|
| (A) | Oil phase | |
| | Liquid paraffin | 53.0 wt. % |
| | White petrolatum | 10.0 |
| | Sample No. 1 | 3.0 |
| | Polyoxyethylene (4 mols) glyceryl ether distearate | 1.5 |
| | Polyoxyethylene (10 mols) oleyl ether | 2.0 |
| (B) | Aqueous phase | |
| | Polyethyleneglycol 600 | 0.5 |

-continued

| Formulation No. 3: | |
|---|---|
| Propyleneglycol | 0.5 |
| Water | balance |

The oil phase (A) was dissolved uniformly at 75° C., to which the aqueous phase (B) warmed to 70° C. was added slowly and cooled to 30° C. under stirring. A cleansing cream was prepared.

| Formulation No. 4: | | |
|---|---|---|
| (A) | Oil phase | |
| | Cetanol | 1.5 wt. % |
| | Sample No. 7 | 0.5 |
| | Stearyldimethylbenzyl ammonium chloride | 2.0 |
| | Glyceryl monostearate | 5.0 |
| (B) | Aqueous phase | |
| | Propyleneglycol | 4.0 |
| | Water | balance |

The oil phase (A) was dissolved uniformly at 70° C., to which the aqueous phase (B) warmed to 75° C. was added slowly and stirring was effected slowly so as not to bring air bubbles. After cooling to 30° C. a hair rinse in form of emulsion was obtained.

| Formulation No. 5: | | |
|---|---|---|
| (A) | Oil base | |
| | Castor oil | 50.0 wt. % |
| | Palmityl alcohol | 10.0 |
| | Bees wax | 10.0 |
| | Ceresin | 10.0 |
| | Liquid paraffin | 5.5 |
| | Candelilla wax | 5.0 |
| | Sample No. 5 | 4.0 |
| | Carnauba wax | 2.0 |
| (B) | Coloring matter | |
| | Titanium oxide | 2.0 |
| | Red coloring matter | 0.5 |
| (C) | Perfumes | small amount |

Oil base (A) was warmed to 80° C., dissolved uniformly, then cooled and kneaded intimately with a roll mill. Thereto were coloring matters (B) added and dissolved uniformly and further perfumes were added. The thus obtained product, after defoaming, was cast to a mold and quenched to obtain a lipstick.

| Formulation No. 6: | | |
|---|---|---|
| (A) | Oil phase | |
| | Liquid paraffin | 20.0 wt. % |
| | White petrolatum | 10.0 |
| | Cetyl alcohol | 20.0 |
| | Sample No. 1 | 4.0 |
| | Polyoxyethylene (15 mols) stearyl ether | 4.0 |
| (B) | Aqueous phase | |
| | Sodium laurylsulfate | 1.0 |
| | Water | 41.0 |

Oil phase (A) was warmed to 70° C. and dissolved uniformly and at the same temperature aqueous phase (B) was added. After emulsification cooling was conducted to obtain an ointment.

What is claimed is:

1. A composition which comprises a mixture of the esterification reaction product between an intermolecular oligo-esterification carboxylic acid of 12-hydroxy stearic acid and/or ricinoleic acid represented by the formula, $$\begin{array}{c} OH \\ | \\ OCO-R_2-CH-R_1 \\ | \\ (OCOR_2-CH-R_1)_n \\ | \\ HOOC-R_2-CH-R_1 \end{array}$$

wherein radical $$R_1-CH-R_2-$$

stands for the alkyl group of 12-hydroxy stearic acid or ricinoleic acid wherein $R_1$ is $-(CH_2)_5CH_3$ and $R_2$ is $-(CH_2)_{10}$ or $-(CH_2)_7CH=CHCH_2-$ and n is 0 or an integer of 1 or more and sterol and an esterification product of 12-hydroxy stearic acid and/or ricinoleic acid with sterol, the latter being included up to 50 weight %.

* * * * *